United States Patent
Murray et al.

(10) Patent No.: US 7,063,781 B2
(45) Date of Patent: Jun. 20, 2006

(54) TECHNIQUES FOR SENSING CHLORIDE IONS IN WET OR DRY MEDIA

(75) Inventors: George M. Murray, Columbia, MD (US); Russell P. Cain, Columbia, MD (US); Bliss G. Carkhuff, Laurel, MD (US); Francis Weiskopf, Catonsville, MD (US)

(73) Assignee: The Johns Hopkins University, Baltimore, MD (US)

( * ) Notice: Subject to any disclaimer, the term of this patent is extended or adjusted under 35 U.S.C. 154(b) by 259 days.

(21) Appl. No.: 10/734,065

(22) Filed: Dec. 11, 2003

(65) Prior Publication Data

US 2004/0118682 A1 Jun. 24, 2004

Related U.S. Application Data

(60) Provisional application No. 60/432,520, filed on Dec. 11, 2002.

(51) Int. Cl.
*G01N 27/333* (2006.01)
(52) U.S. Cl. .................. 205/789; 205/775.5; 204/418; 204/404
(58) Field of Classification Search ................ 204/416, 204/418, 404; 205/778.5, 779, 775.5, 777, 205/789
See application file for complete search history.

(56) References Cited

U.S. PATENT DOCUMENTS 5,766,934 A * 6/1998 Guiseppi-Elie .......... 435/287.9

OTHER PUBLICATIONS

Sjöberg et al. (All-Solid-State Chloride-Selective Electrode Based on Poly(3-octylthiophene) and tridodecylmethylammonium Chloride, Electroanalysis 1999, 11, No. 10-11).*
Dong S., Sun, Z., and Lu, Z., "Chloride Chemical Sensor Based on an Organic Conducting Polypyrrole Polymer," The Analyst, vol. 113, Issue 10, pp. 1525-1528, London, 1988.

* cited by examiner

*Primary Examiner*—Alex Noguerola
(74) *Attorney, Agent, or Firm*—Albert J. Fasulo, II

(57) ABSTRACT

Techniques are provided for measuring chloride ion concentration in a medium. The techniques allow measurements to be made in dry or alkaline media, or both. For alkaline conditions, a sensor includes a pair of electrodes and a polymer film imprinted for uptake of chloride ions under alkaline conditions. The film is deposited to be in contact with at least one electrode and the medium. For dry conditions, a sensor includes a pair of electrodes and a conductive polymer film imprinted for uptake of chloride ions. The film is in contact with the pair of electrodes, and is positioned for contact with the medium. An electrical conductivity of the film depends on an amount of chloride ions taken up by the film. Some techniques allow chloride ion measurements over years at sensors embedded in concrete. Such measurements allow the determination of the progress of rebar corrosion in concrete infrastructure.

24 Claims, 12 Drawing Sheets

210
PYRROLE

220
POLYPYRROLE

230
METHYLPYRROLE

240
POLY METHYLPYRROLE

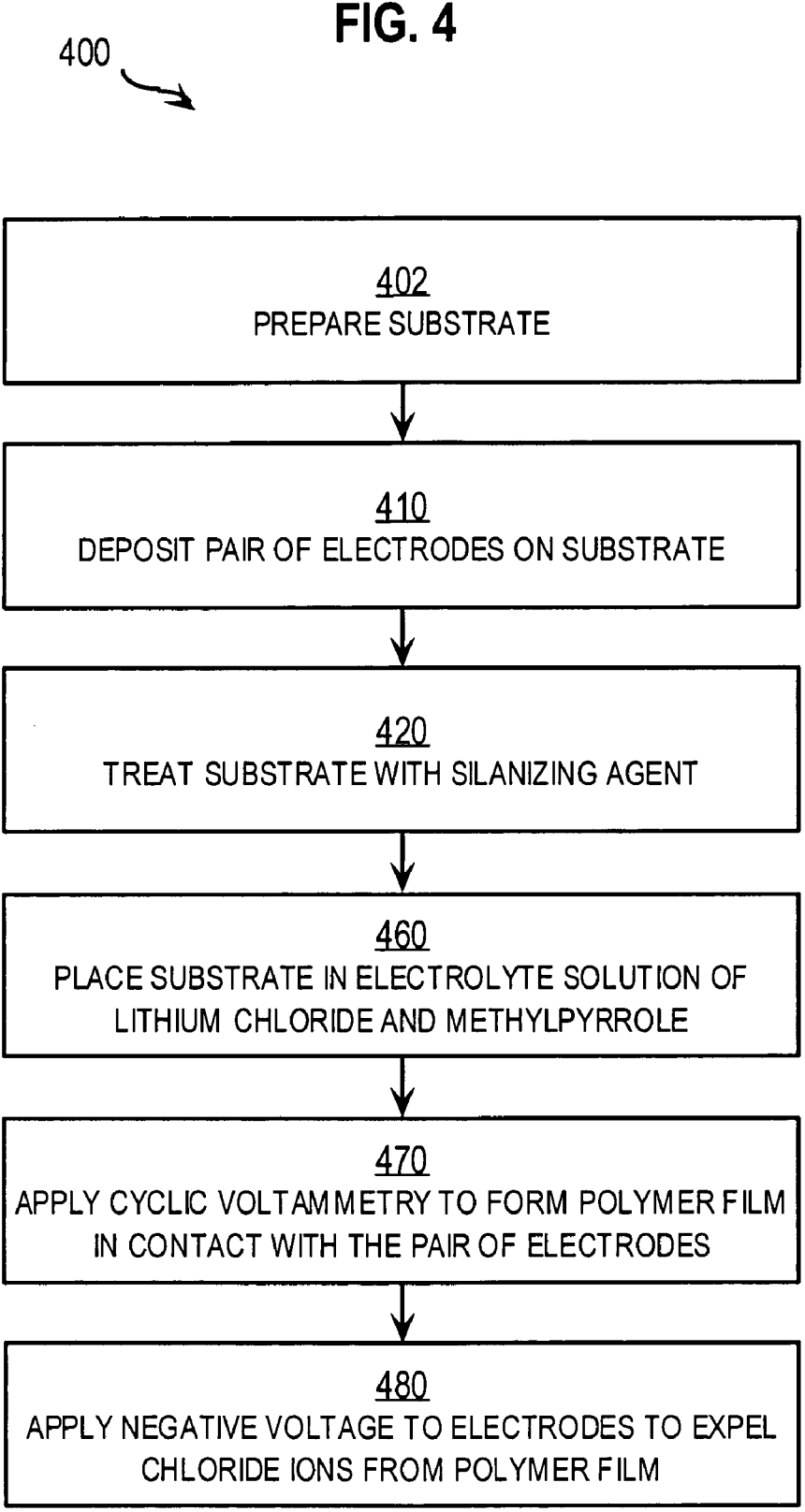

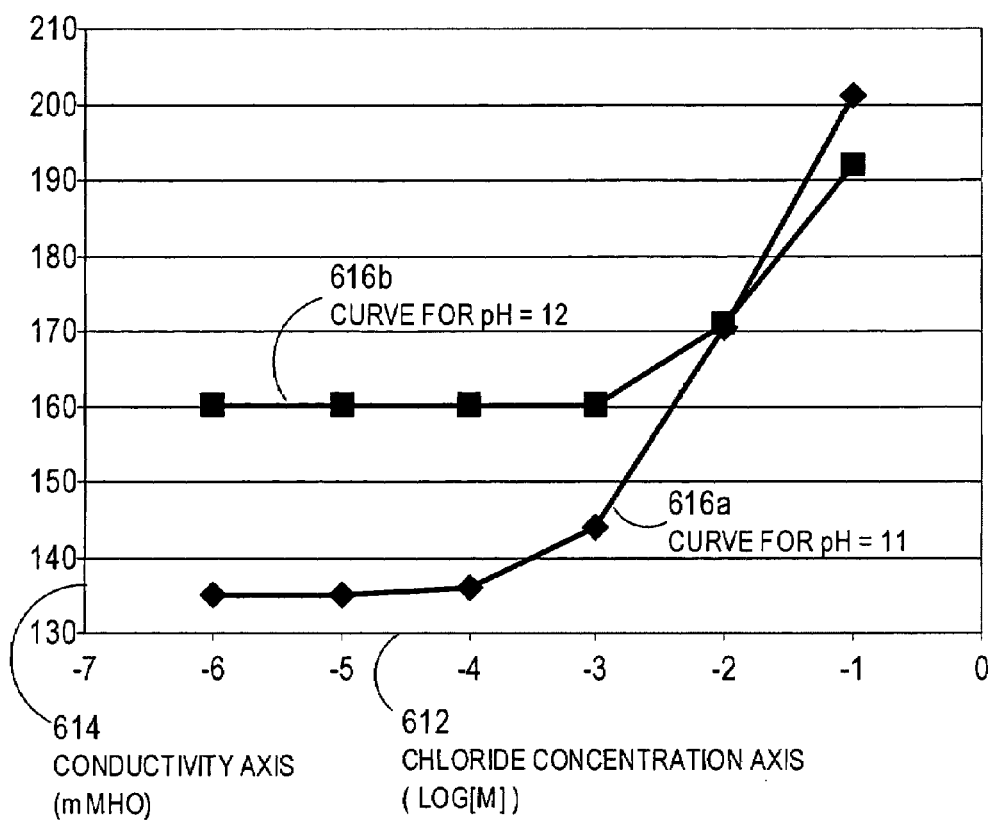

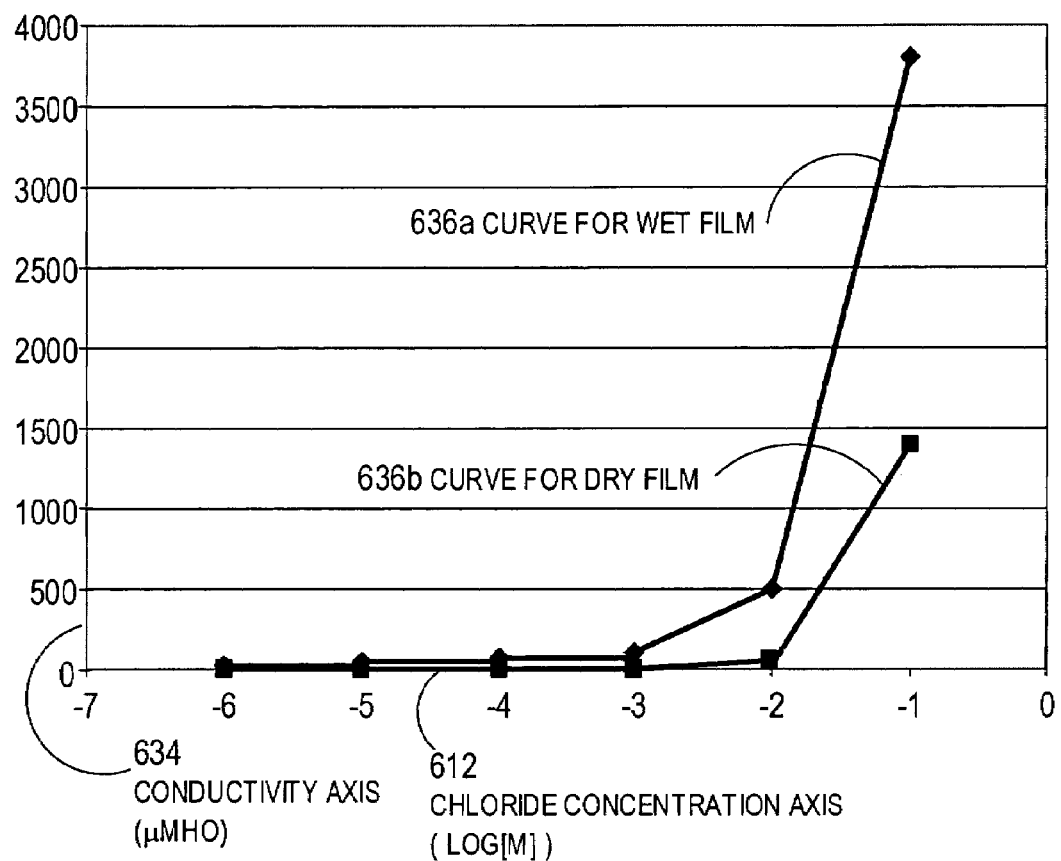

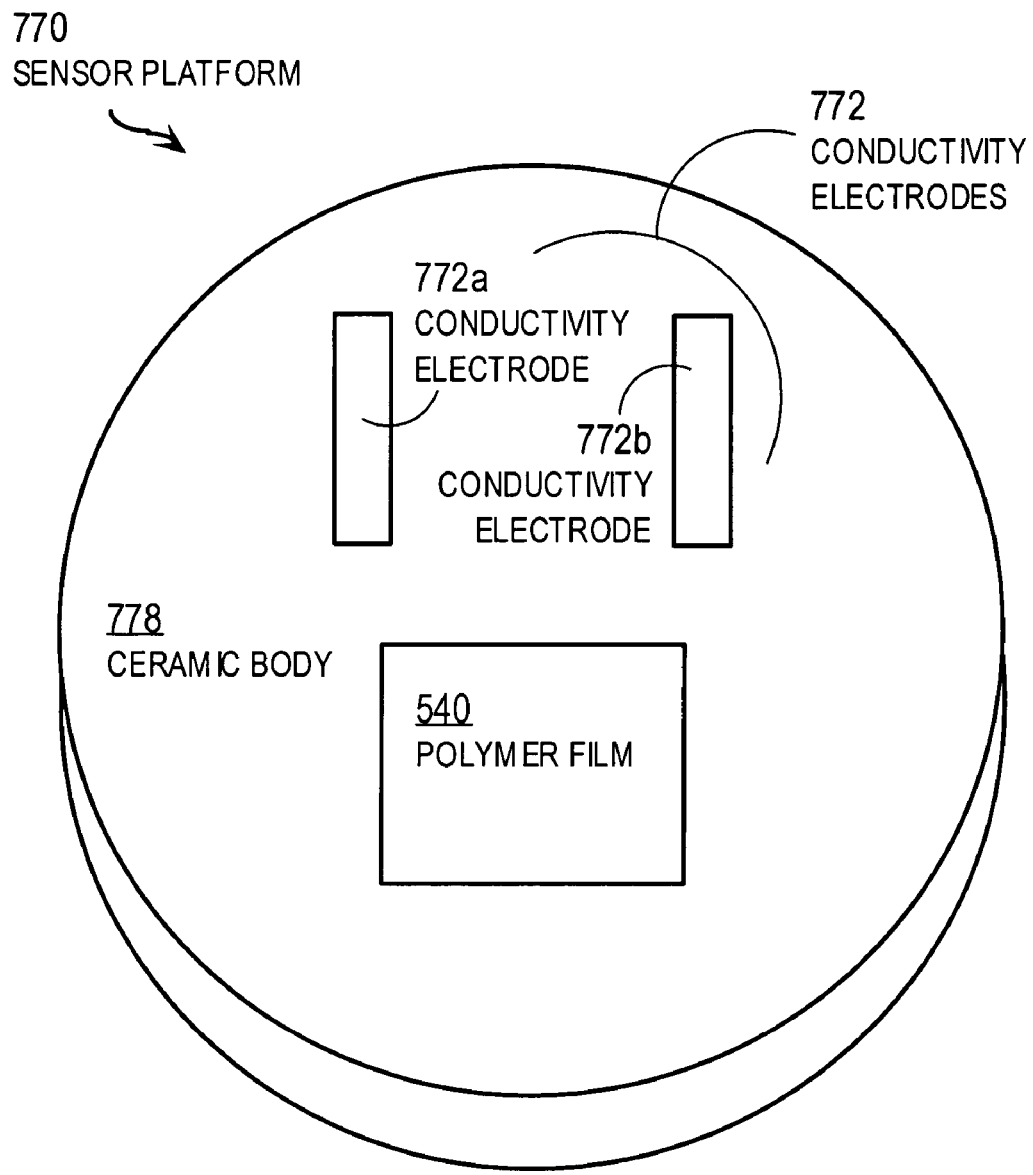

TECHNIQUES FOR SENSING CHLORIDE IONS IN WET OR DRY MEDIA

CROSS-REFERENCE TO RELATED APPLICATIONS

This application claims benefit of Provisional Application 60/432,520, filed Dec. 11, 2002, under 35 U.S.C. §119(e).

BACKGROUND OF THE INVENTION

1. Field of the Invention

The present invention relates to a sensor, an apparatus incorporating the sensor and a method of fabricating the sensor to measure chloride ions; and in particular to measuring chloride ions in difficult conditions, such as varying wet and dry conditions in structural concrete with high pH for a duration of years.

2. Description of the Related Art

The United States is replacing aging infrastructure (such as buildings, bridges and piers) and simultaneously developing the tools and techniques to monitor new infrastructure as it ages. In particular, the US Department of Transportation and other organizations are developing approaches to monitor these structures in order to manage their maintenance and rehabilitation.

Currently, trained personnel base most infrastructure monitoring on individual sensor measurements or periodic visual inspection. These measurements are not distributed throughout the structure being monitored; they are used only as sparse samples to assess general health of the structure. The structure is not thoroughly sampled, mostly due to economic limitations. The cost of these measurements is high because of installation and monitoring requirements. This approach doesn't detect degradation until it has already reached an advanced state. When advanced degradation does occur, the corrective actions are more expensive than if the progress of degradation had been detected at a less advanced stage. Additional costs are incurred because the resources consumed to repair a highly degraded structure diminish scheduled repairs and maintenance for other structures. In addition, costs are imposed on the users of those structures, as their travel or utilization is diverted for extended periods of time.

In a recent approach, a robust, reliable, long-lasting and cost-effective instrumentation package is embedded in the infrastructure to measure the parameters of the physical processes that cause the degradation. The goal is to monitor the physical parameters so that a degrading environment can be detected and maintenance or remediation implemented early—before advanced degradation actually occurs. By focusing on measuring the physical processes at a large number of locations in the structure being monitored, the environmental states associated with the processes can be detected, and even relatively localized areas of degradation can be determined. When monitored at different times, these can be used to indicate the evolution of the infrastructure environment with time. Detecting the onset and evolution of the processes causing the degradation enables corrective action to be scheduled and implemented before significant degradation occurs. Such early remedial action is less expensive and disruptive than the more costly and time-consuming repair or replacement required after advanced degradation.

For example, in bridge decks, corrosion of rebar is the primary cause of degradation. Corrosion is accelerated as salt water is transported through the concrete. Salt water includes constituents such as sodium chloride, NaCl. Salt water originates in thaw water on structures that have been de-iced with salt and on seaboard structures subject to salt spray from the ocean or other body of salt water. Empirical relationships for corrosion rate based on concrete electrical conductivity and other environmental parameters including chloride ion concentration have been developed. These conductivity relationships are interpreted to represent a host of transport properties that result in corrosion and the relationships have considerable scatter. Thus, conductivity has value as a gross indicator of the probability of corrosion but only in the context of field measurements taken in particular environments. In particular, it has been found that corrosion rate is independent of conductivity without the presence of chloride ion. Since the presence of chloride ion plays an essential role in rebar corrosion, a measure of chloride ion concentration provides a strong indication of the corrosive environment of a structure. For such cases, the recent approach is based on set of embedded sensors including temperature, conductivity and chloride ion, among others.

A well-known chloride ion sensor is based on silver (Ag) electrodes with silver—chloride (AgCl) coating, called Ag/AgCl wire electrodes. The sensor functions due to the sparingly soluble nature of AgCl.

While suitable for many purposes, a sensor based on Ag/AgCl wire electrodes suffers from some disadvantages. One disadvantage is that the longevity of the Ag/AgCl wire electrodes is limited to about three months of operation when imbedded in concrete, well short of the decades of life desirable for monitoring bridge decks. The functionality of the silver electrodes is of limited duration due to the high pH (alkalinity) in concrete. Analysis of the chemical processes associated with Ag/AgCl electrodes in concrete indicates that the likely failure mode is erosion of the AgCl to form silver hydroxide (AgOH). At high values of pH, large concentrations of hydroxide ion ($OH^-$) exist. Hydroxide also forms a sparingly soluble compound with silver, AgOH. The thin coatings of AgCl are likely to degrade with the repeated attack of large amounts of hydroxide.

Another disadvantage of the sensor based on Ag/AgCl wire electrodes is that it is insensitive to low chloride ion concentrations. A further disadvantage is that the Ag/AgCl wire electrodes must be wet, in order that environmental chloride ions are mobile between the electrodes at the time of the measurement. This is a disadvantage for making measurements in concrete that is dry. Concrete in infrastructures is often dry at times when it is convenient to make measurements, and concrete at several inches from the surface may be dry even after many rain events. A further disadvantage is that the electrodes are formed as wires that extend into the medium. Such extensions are easily damaged during a process to embed the sensors in the medium. Further disadvantages occur under freezing conditions. The Ag/AgCl electrode requires a reference electrode that usually has some sort of electrolyte inside. Upon freezing this electrolyte precipitates its ionic constituents; and those constituents may not re-dissolve well. Also, as with no moisture, frozen moisture does not allow mobile ions that provide a conductive path to support a voltage measurement between electrodes.

Another approach for measuring chloride ions is described in an article by Shaojun Dong, Zhisheng Sun and Ziling Lu, "Chloride Chemical Sensor Based on an Organic Conducting Polypyrrole Polymer", ANALYST, vol. 113, October 1988, (hereinafter Dong) the entire contents of which are hereby incorporated by reference as if fully set forth herein. This approach determines ion concentration based on potential difference between a reference electrode and an electrode coated with a particular polymer selective for the chloride ion. Dong demonstrated that a chloride-ion-selective electrode could be made by electro-polymerization of pyrrole with a supporting electrolyte solution of 0.1 M LiCl. The reason that this happens, though not explained in the article, is that the approach effectively employs chloride imprinting of cross-linked polymers. Polypyrrole is an extensively cross-linked polymer. Electro-polymerization of polypyrrole results in over oxidation that yields an average of one positive charge distributed over four pyrrole units. This positive charge is compensated in this case by chloride anions. By forming the polymer in this manner, the polymer has essentially become molecularly imprinted for chloride ion. Application of a negative potential to the chloride polymer will cause it to expel chloride ions. Use of the polymer-coated electrode in an electrochemical cell allowed the selective measurement of chloride ion, proving that some form of imprinting had occurred.

While suitable for many purposes, the approach of Dong also suffers some disadvantages. One disadvantage is that the reference electrode and polymer-coated electrode must be wet. As stated above, this is a disadvantage for making measurements in concrete that is often dry. A second disadvantage is that the sensor is not designed for the high alkaline levels found in concrete (pH greater than 10). As stated in Dong, the sensor response is relatively constant in acidic to neutral solutions (pH 2.5 to 7) but tails off at higher pH levels. A third disadvantage is that the electrodes are formed as wires that extend into the medium and are easily damaged during a process to embed the sensors in the medium.

Based on the foregoing description, there is a clear need for techniques for measuring chloride ion concentration that do not suffer the disadvantages of the prior art chloride ion sensors. For example, there is a need for chloride sensors that measure chloride ion concentrations in a wet or dry medium. There is also a need for chloride sensors that measure chloride ion concentrations in highly alkaline conditions.

In particular, there is a need for long-lived chloride sensors that measure chloride ion concentrations significant for determining multiple degrees of rebar corrosion in reinforced concrete whether the concrete is wet or dry at the time of the measurement.

SUMMARY OF THE INVENTION

Techniques are provided for measuring chloride ions in a medium. In various embodiments, the techniques allow measurements to be made in wet or dry media under alkaline as well as acidic conditions. Among other applications, these embodiments allow chloride ion concentrations to be measured over several years at sensor platforms that are embedded in concrete for determining the progress of rebar corrosion in the concrete.

According to one aspect of the invention, a sensor for measuring chloride ion concentration in a medium includes a pair of electrodes and a polymer film imprinted for uptake of chloride ions under alkaline conditions. The film is deposited to be in contact with at least one electrode of the pair and for contact with the medium.

According to an embodiment of this aspect, the film includes methylpyrrole.

According to an embodiment of this aspect, the film is in contact with both electrodes of the pair.

According to another aspect of the invention, a sensor for measuring chloride ion concentration in a medium includes a pair of electrodes and a conductive polymer film imprinted for uptake of chloride ions. The film is in contact with the pair of electrodes, and is positioned for contact with the medium. An electrical conductivity of the film depends on an amount of chloride ions taken up by the film.

According to another aspect of the invention, a sensor for measuring chloride ion concentration in a medium includes a pair of electrodes and a conductive polymer film imprinted for uptake of chloride ions under alkaline conditions. The film is in contact with the pair of electrodes, and is positioned for contact with the medium. An electrical conductivity of the film depends on an amount of chloride ions taken up by the film.

According to another aspect of the invention, an apparatus for long term monitoring of chloride ion concentration in a medium includes a sensor platform for embedding in a medium. A transmitter is attached on the sensor platform for transmitting to an interrogation unit a response signal based on a chloride measurement. A chloride sensor is attached on the sensor platform for generating the chloride measurement. The chloride sensor includes a pair of electrodes and a conductive polymer film imprinted for uptake of chloride ions under alkaline conditions. The film is in contact with the pair of electrodes, and the film is positioned for contact with the medium. An electrical conductivity of the film depends on an amount of chloride ions taken up by the film.

According to an embodiment of this aspect, a conductivity sensor is also included on the platform for generating an electrical conductivity measurement of the medium. The response signal is further based on the conductivity measurement.

According to another aspect of the invention, a method for fabricating a chloride sensor includes depositing an electrode on a substrate, and then placing the substrate in an electrolyte solution of lithium chloride and methylpyrrole. Cyclic voltammetry is then applied to form a polymer film in contact with the electrode.

According to another aspect of the invention, a method for fabricating a chloride ion sensor includes depositing a pair of electrodes on a substrate. The substrate is treated with a silanizing agent to enhance adherence of pyrrole to the substrate between the pair of electrodes. After treating the substrate with a silanizing agent, the substrate is placed in an electrolyte solution of lithium chloride and pyrrole. Then cyclic voltammetry is applied to form a polymer film in contact with the pair of electrodes.

BRIEF DESCRIPTION OF THE DRAWINGS

The present invention is illustrated by way of example, and not by way of limitation, in the figures of the accompanying drawings in which like reference numerals refer to similar elements and in which:

FIG. 4 is a flow diagram that illustrates a method for fabricating a chloride ion sensor, according to an embodiment;

FIG. 6A is a graph that illustrates the performance of a chloride ion sensor at different pH levels, according to an embodiment;

FIG. 6C is a graph that illustrates the performance of a chloride ion sensor under wet and dry conditions, according to an embodiment;

FIG. 7B is a block diagram that illustrates an outer face of a sensor platform to be embedded in a medium for measuring chloride ion concentration, according to an embodiment.

DETAILED DESCRIPTION

Figure 1:
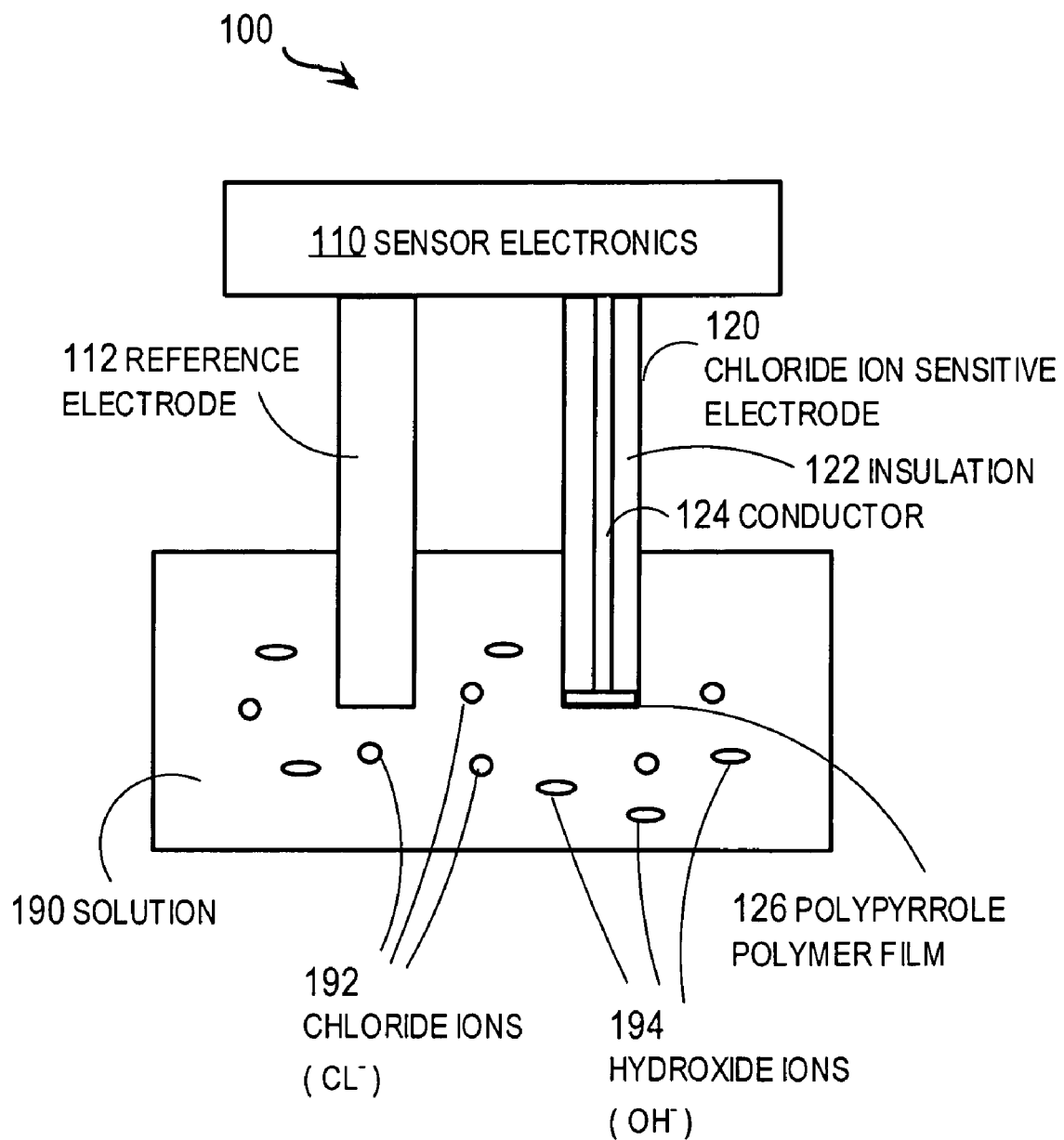
FIG. 1 is a block diagram that illustrates a sensor for measuring chloride ion concentration in a solution, according to an embodiment.
Figure 2A:
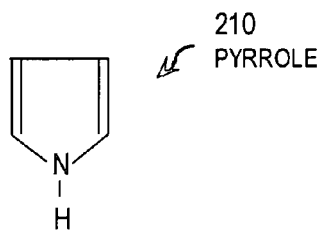
FIGS. 2A, 2B, 2C, 2D are chemical diagrams that illustrate a pyrrole molecule, a portion of a polypyrrole chain, a methylpyrrole molecule, and a portion of a poly-methylpyrrole chain, respectively.
Figure 2B:
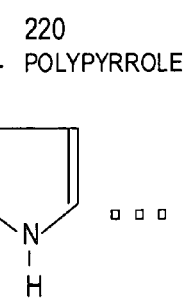
Figure 2C:
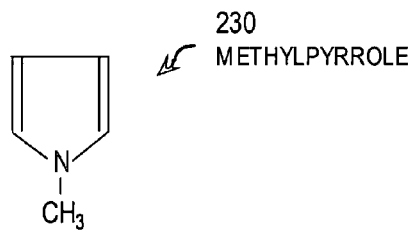
Figure 2D:
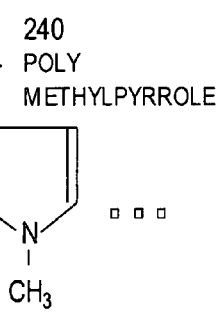

Techniques are described for measuring chloride ions in a medium. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Particular embodiments of the invention are described in the context of measuring chloride ions in reinforced concrete decks of structures such as bridges and piers. However, the invention is not limited to this context, and embodiments may be deployed to measure chloride ion concentrations in solutions, in gases such as air, and at other solid media, such as in non-reinforced concrete or on steel girders.

In the concrete context, it is desirable that the sensitivity of the chloride ion sensor be sufficient to determine multiple degrees of corrosion. Table 1 lists chloride ion concentration levels of interest in the context of reinforced concrete. In other contexts, other concentration levels are likely to be of interest.

In Table 1, chloride ion concentrations are related to corrosion by four different authorities. Rules promulgated by the Maryland State Highway Authority are indicated by the acronym MDSHA. A rule promulgated by the Federal Highway Administration is indicated by the acronym FHWA. A building code promulgated by the American Concrete Institute is indicated by the acronym ACI. A rule promulgated by the California Department of Transportation is indicated by the acronym CalDOT. Equivalent concentrations in solution are expressed in units of Molarity (M).

TABLE 1

Significant concentrations of Cl— in concrete.

| Classification Source | Corrosion Classification | Concentration (pounds NaCl per cubic yard) | Concentration (percent Cl— by weight) | Equivalent Concentration in Solution (M) |
|---|---|---|---|---|
| MDSHA | No corrosion | <1.2 | <0.0293 | <0.0122 |
| MDSHA | Moderate corrosion | 1.2 to 2.0 | 0.0293 to 0.0490 | 0.0122 to 0.0203 |
| MDSHA | Significant corrosion | >2.0 | >0.0490 | >0.0203 |
| FHWA | Corrosion | >1.4 | >0.0342 | >0.0142 |
| ACI | Corrosion | 3.65 | 0.0910 (0.15% NaCl by mass) | 0.0371 |
| CalDOT | Corrosion | 3.25 | 0.0794 | 0.033 |

The classifications in Table 1 are defined at relatively high concentration levels; therefore relatively low sensor accuracy is expected to be sufficient. Different levels of corrosion can be determined with an accuracy of about 0.01 percent by weight. To determine temporal changes in chloride concentration in the "No corrosion" classification, i.e., before there is noticeable corrosion, a minimum detectable concentration should be small compared to 0.0293 pounds NaCl per cubic yard. For purposes of illustration, it is assumed that a maximum detectable concentration of 1.4 pounds per cubic yard is useful, corresponding to 0.0342 percent by weight and 0.0142 M. If this change is associated with all 8 bits of an 8 bit value from an analog to digital (A/D) converter, then a useful minimum detectable concentration difference is 0.0055 pounds per cubic yard, corresponding to 0.00013 percent by weight and $0.55 \times 10^4$ M.

The pH levels in reinforced concrete are high. Unset concrete has a pH of no more than 12.65. The pH of concrete decreases slowly as the concrete cures but remains above about 10.

1. Measurements of Chloride Ion at High pH

FIG. 1 is a block diagram that illustrates a sensor 100 for measuring chloride ion concentration in a solution 190, according to an embodiment. The solution 190 includes a concentration of chloride ions (Cl—), such as ions represented by circles 192. The solution 190 includes a concentration of hydroxide ions (OH—) that depends on the pH of the solution, such as hydroxide ions represented by ellipses 194.

The sensor 100 includes sensor electronics 110 and two electrodes. One electrode is a reference electrode 112 and the other electrode 120 is a chloride-ion-sensitive electrode 120. The electrical potential response of the reference electrode 112 depends on the concentration of ions in the solution 190, but not on the concentration of any particular ion. The chloride-ion-sensitive electrode 120 has an electric potential response that depends on the concentration of chloride ions 192 in the solution 190. The sensor electronics 110 are configured to output a response that depends on the electrical potential difference between the two electrodes 112, 120.

The chloride-ion-sensitive electrode 120 includes a polymer film 126 deposited on a conductor 124, such as glassy carbon. The portion of the conductor without the polymer film 126 is covered by an electrical insulator 122, such as glass. The polymer has an electric potential response that depends on the concentration of chloride ions 192 in the solution 190.

According to Dong, the polymer film is polypyrrole deposited on the glassy carbon from a solution of pyrrole (Py) and lithium chloride (LiCl) using an electrochemical polymerization process, well known in the art. The electro-chemical polymerization process is described in more detail, for example, in B. J. Feldman, P. Burgmayer, and R. W. Murray, "The potential dependence of electrical conductivity and chemical charge storage of poly(pyrrole) films on electrodes," J. Am. Chem. Soc., vol. 107, 4, pp. 872–878, 1985, and J. R. Reynolds, P. A. Poropatic, and R. L. Toyooka, "Electrochemical copolymerization of pyrrole with N-substituted pyrroles—Effect of composition on electrical conductivity," Macromolecules, vol. 20, 5, pp. 958–961, 1987, the entire contents of each of which are hereby incorporated by reference, as if fully set forth herein. Electro-chemical polymerization is carried out using cyclic voltammetry. The thickness of the film is controlled by the polymerization time, the number of scans, and the applied potential during the cyclic voltammetry process, among other conditions.

As reported by Dong, the sensor response decreases with increasing alkalinity above neutral conditions (a pH about 6). It is expected that the electrodes are subject to attack by excess hydroxide ions 194 at the high alkaline levels. According to embodiments of the invention, the polymer film 126 includes methylpyrrole to resist the attack of hydroxide ions.

FIGS. 2A, 2B, 2C, 2D are chemical diagrams that illustrate a pyrrole molecule 210, a portion of a polypyrrole chain 220, a methylpyrrole molecule 230, and a portion of a poly-methylpyrrole chain 240, respectively. In pyrrole molecules and polypyrrole chains, a Nitrogen atom (N) is bound to a Hydrogen atom (H). In methylpyrrole molecules and poly-methylpyrrole chains, the Nitrogen atom (N) is bound to a methyl group ($CH_3$). At high pH, which indicates an excess of hydroxide ions (OH—), the methyl group is expected to be more resistant to attack by hydroxide ions. The absence of a proton on methylpyrrole makes the polymer less acidic and therefore the conductivity would be less influenced by higher concentrations of base.

Therefore, according to some embodiments, the polymer film is chloride-ion-imprinted poly-methylpyrrole deposited on the conductor from a solution of poly-methylpyrrole (nMPy) and lithium chloride (LiCl) using an electro-chemical polymerization process.

2. Measurements of Chloride Ion in Dry Media.

Measuring chloride ion concentration based on a potential difference between two electrodes in a solution requires that the medium be sufficiently wet between the two electrodes so that ions can migrate as in a solution. As described above, the medium is not always wet when it is convenient or desirable to make a measurement. Therefore it is often useful to have a sensor that can provide chloride ion concentrations when the medium is dry.

For example, in the case of reinforced concrete, the chloride ions migrate through a penetration depth in the concrete during soakings with salty water (such as from thawing of salted ice or spray from a body of salt water). The chloride ions are left behind when the concrete dries. Cracks and other defects in the concrete extend the penetration depth of soakings. Corrosion occurs when the chloride ions contact the iron reinforcement bars (rebar) in the concrete. The concrete is often dry when it is desirable to make the measurement of chloride ion concentration.

Figure 3:
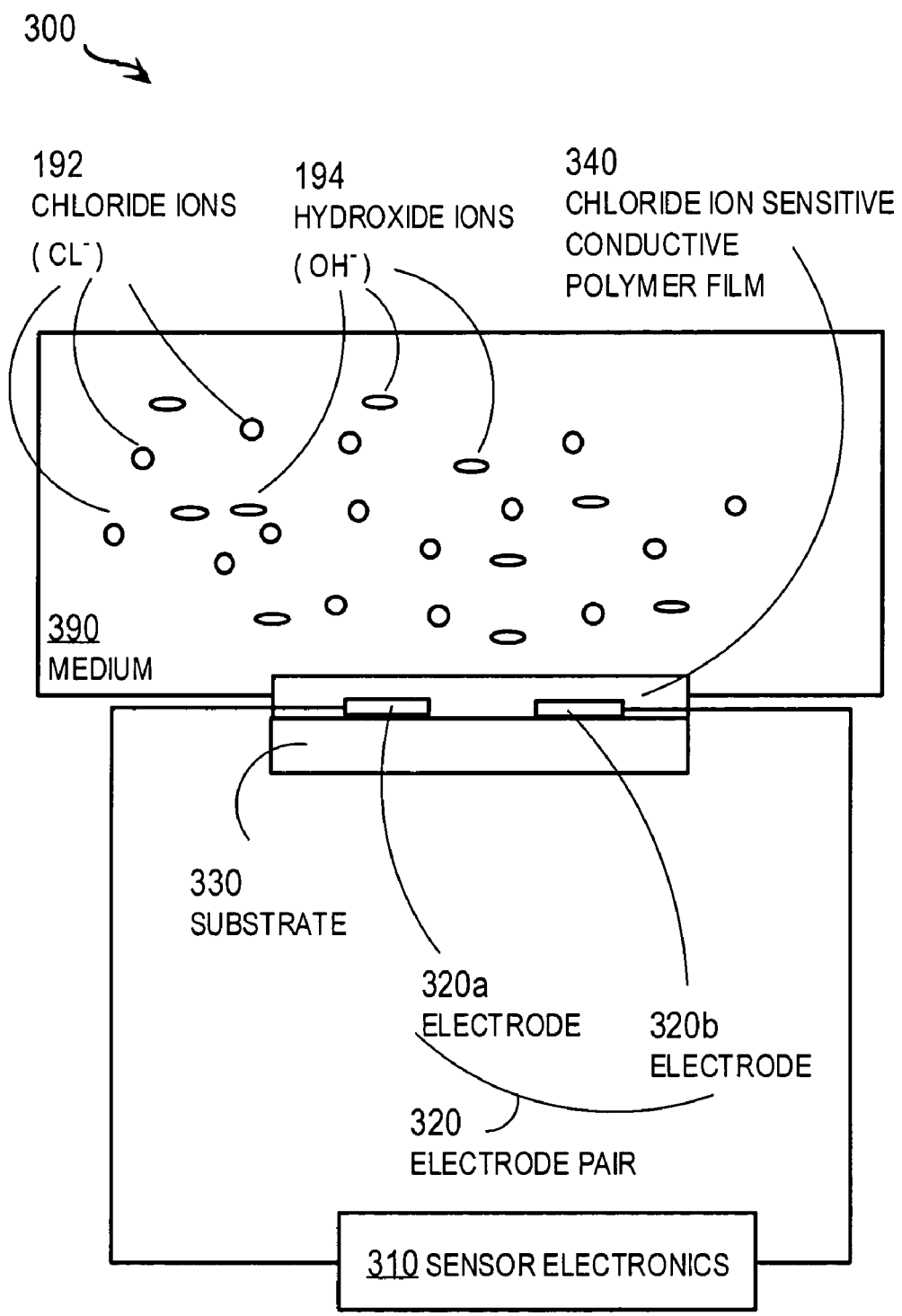
FIG. 3 is a block diagram that illustrates a sensor for measuring a chloride ion concentration in a dry medium, according to an embodiment.

For measurement during dry conditions, a conductive polymeric film that exhibits selectivity for chloride ion is used as a chloride ion sensor. FIG. 3 is a block diagram that illustrates a sensor 300 for measuring a chloride ion concentration in a dry medium 390, according to an embodiment. This sensor also works when the medium 390 is wet.

The medium 390 includes a concentration of chloride ions (Cl—), such as ions represented by circles 192. The medium 390 includes a concentration of hydroxide ions (OH—) that depends on the pH of the medium, such as hydroxide ions represented by ellipses 194.

The sensor 300 includes sensor electronics 310 and a pair of electrodes 320 deposited on an electrically insulating substrate. The electrode pair 320 is in electrical contact with a chloride-ion-sensitive conductive polymer film 340. The film is disposed between the electrodes and the medium so that the electrodes do not contact the medium. The film 340 is conductive with an electrical conductivity that depends on the amount of chloride ions absorbed by the film 340. The amount of chloride ions absorbed depends on the concentration of chloride ions in the medium in the vicinity of the film. Therefore the conductivity of the assembly of electrodes, film and substrate depends on the concentration of chloride ions in the medium in the vicinity of the film. The sensor electronics 310 are configured to output an electric signal that depends on the conductivity of the assembly of electrodes, film and substrate. For example, a voltage is applied between electrodes 320a and 320b and a current is measured with an ammeter to determine the electrical conductivity of the assembly by Ohms Law. In another embodiment, an electric current is passed from electrode 320a through film 340 into electrode 320b and a voltage between electrodes 320a and 320b is measured with a voltmeter to determine the electrical conductivity of the assembly by Ohms Law. Because the electrodes are not in contact with the medium, the conductivity of the assembly depends on the conductivity of the film, which depends on the chloride ion concentration.

For example, in an application to a reinforced concrete medium, if salt water soaks to the film, then chloride ions will migrate into the film. When the concrete dries, the chloride ions that migrated into the film remain in the film. A conductivity measurement of the assembly indicates conductivity through the film, which indicates the concentration of chloride ions in the vicinity of the film and therefore an extent of the degradation process in the concrete.

In one embodiment, the film is a chloride-imprinted poly-pyrrole film as described in Dong. In another embodiment, the film is a chloride-imprinted poly-methylpyrrole film that is effective under alkaline conditions.

During fabrication of the assembly in some embodiments, after deposition of the film on the electrodes and substrate, surface chloride ions in the film are expelled by applying a negative voltage to both electrodes while the film is wet. The expelled chloride ions leave behind binding sites in the surface of the film for selective uptake of chloride ions from the medium. The sites have shapes and charge distributions defined by the cross-linked chains into which the expelled chloride ions had formerly fit during the electrochemical polymerization. Other anions of similar size and charge distribution may also bind to these sites, but such anions appear in negligible concentrations in concrete.

In another embodiment, the film is a chloride-imprinted polypyrrole and polystyrene sulfonate film. The polystyrene sulfonate is an anionic polymer that improves the physical characteristics of the film, such as toughness and adhesion, among others. It is not in itself conductive so that including polystyrene sulfonate results in a less conductive sensor. However, the lower conductivity is easier to measure in some embodiments.

3. Fabrication of Chloride Ion Sensor.

FIG. 4 is a flow diagram that illustrates a method 400 for fabricating a chloride ion sensor, according to an embodiment. In the illustrated embodiment, the chloride ion sensor is effective under acidic and alkaline conditions and in wet and dry media. In other embodiments one or more steps may be omitted or replaced or performed in a different order or overlapping in time.

In step 402, a substrate of insulating material is prepared. For example a disk of a glassy carbon is formed, polished and cleaned. In an illustrated embodiment, step 402 includes forming silica glass ($SiO_X$) on an alumina ceramic (96% $AlO_2$) plate. The size of the substrate is selected as appropriate for the platform on which the sensor is to be deployed. For example, in an illustrated embodiment, described in more detail in a later section, a vehicle for deploying the chloride ion sensor is a Wireless Embedded Sensor Platform (WESP). For WESP, the surface area of the substrate is 2.21 $cm^2$ (cm=centimeter).

Figure 5A:
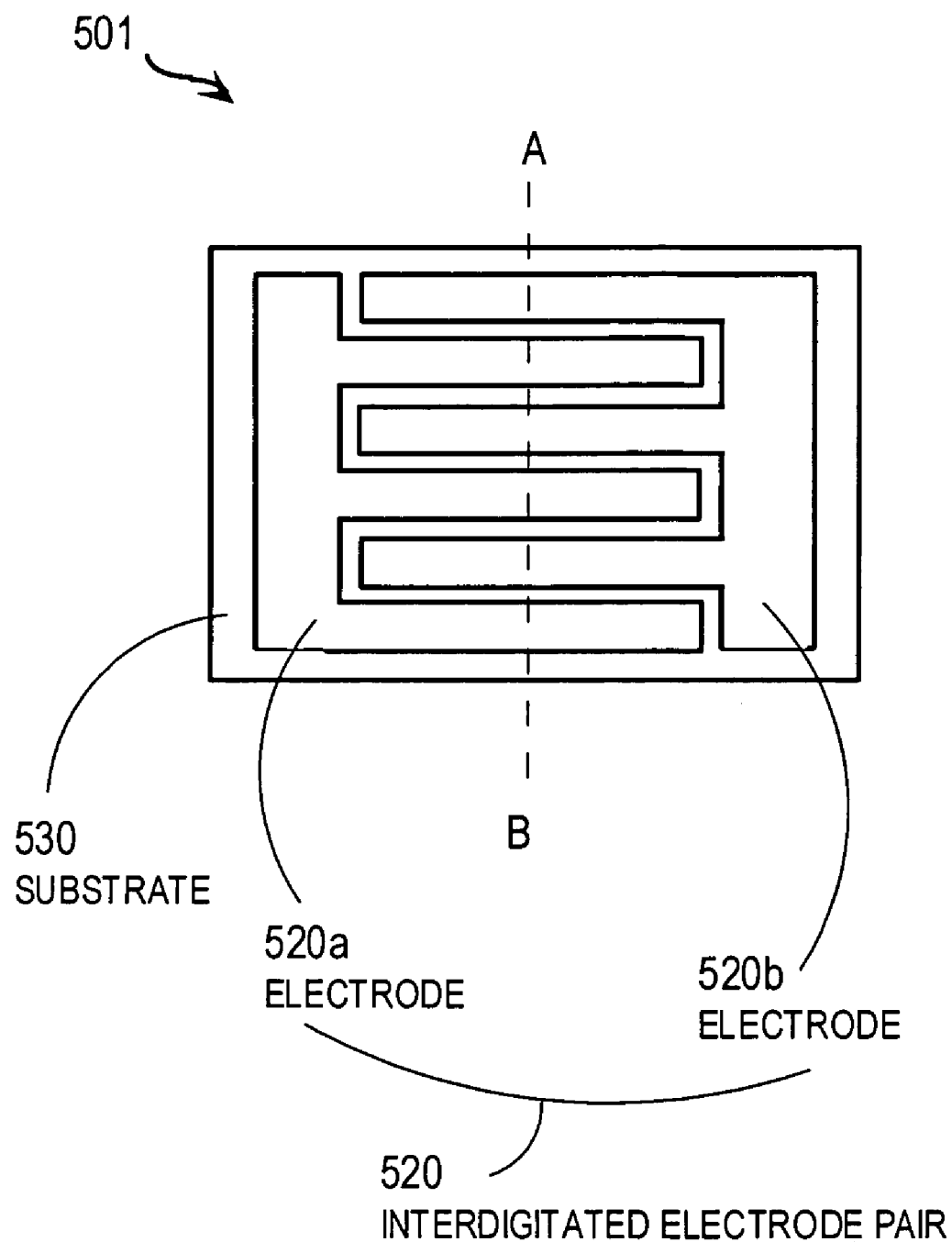
FIG. 5A is a block diagram that illustrates a pair of interdigitated electrodes on a substrate, according to an embodiment.

In step 410, a pair of electrodes is deposited on the substrate. Any method known in the art for depositing the electrodes may be used, such as sputtering of metals. In the illustrated embodiment, interdigitated electrodes are deposited to provide a large area for sampling the conductivity of the film. FIG. 5A is a block diagram that illustrates a pair of interdigitated electrodes on a substrate, according to an embodiment of an electrode assembly 501. The electrode assembly 501 includes a pair of electrodes 520 on substrate 530. As can be seen in FIG. 5A, extensions ("digits" or "fingers") of electrode 520a project between extensions of electrode 520b. This increases the area of film where the conductivity of the film affects the conductivity between the electrodes 520a, 520b without increasing the distance between the electrodes 520a, 520b. In one embodiment, the electrodes 520 are gold. In the illustrated embodiment, each electrode 520a, 520b has three extensions. Line AB indicates the position of a cross sectional plane through the electrode assembly. In other embodiments, each electrode may have more or fewer extensions and different relative dimensions of width, extensions, separation, and other features.

In some embodiments, step 410 includes cleaning the electrode assembly 501. For example, the electrode assembly 501 is rinsed with isopropyl alcohol and subjected to cyclic voltammetry in a 0.1 M hydrochloride (HCl) solution using cyclic voltammetry to remove species that are not native to the surface and prepare the surface for deposition of the polymer film. The 0.1 M HCl solution is formed by diluting a 1 M stock HCl solution prepared from reagent grade HCl, from Fisher Scientific of Pittsburgh, Pa., in de-ionized water and de-aerating by bubbling nitrogen gas ($N_2$) through the solution for ten minutes. Cyclic voltammetry is performed on a CS-1200 potentiostat from Cypress Systems of Lawrence, Kans. During cleaning, scanning parameters were set for 100 to 1800 millivolts (mV, 1 $mV=10^{-3}$ Volts) at 50 mV per second (mV/s) with a current of 200 microamperes ($\mu A$, 1 $\mu A=10^{-6}$ Amperes).

In step 420 the electrode assembly is treated with a silanizing agent. The silanizing agent enhances adherence of pyrrole species, including pyrrole and methylpyrrole, to the non-conducting substrate between the electrodes during a later electro-chemical polymerization step, described below. The silanizing agent also serves to make the surface between electrodes less hydrophilic and more hydrophobic. For example, in an illustrated embodiment, step 420 includes placing the electrode assembly 501 in a bath with a silanizing agent that includes pyrrole, silica (Si), and ($CH_3O$). In one embodiment, silanization is performed using a 10% (w/v) solution of N-(3-trimethoxysilylpropyl) pyrrole, from Gelest Inc., Morrisville, Pa., in 95% ethanol. The substrate is immersed in the solution from 2 to 5 minutes, and allowed to dry in air for 24 hours. The successful application of the silanized coating is verified if a water droplet beads up on the surface.

In some embodiments, step 420 is omitted. For example, in embodiments for use only in solutions with a configuration as shown in FIG. 1, the film is deposited only on an electrode and need not adhere to a non-conducting substrate.

In step 460, the electrode assembly is placed in an electrolyte solution of a chloride salt and a pyrrole species. In an illustrated embodiment, the solution includes 1M LiCl and 0.1M nMPy in de-ionized water and is de-aerated by bubbling $N_2$ through the solution for ten minutes. The LiCl and nMPy are obtained from Aldrich Chemical Company of Milwaukee, Wis. In other embodiments, other concentrations of chloride salts and pyrrole are used. The exact concentrations are determined as a matter of design choice for the properties, such as conductivity sensitivity and pH resistance, of the polymer film to be deposited. The properties of the polymer film for different example choices of the electrolyte solution are described in a later section.

In step 470, cyclic voltammetry is applied to form a chloride ion doped polymer film in contact with and covering at least one of the pair of electrodes during electrochemical polymerization. In the illustrated embodiment, this step is performed to cover both electrodes and the intervening substrate. In the illustrated embodiment, this step employs cyclic voltammetry in the CS-1200 with scanning parameters set from 800 mV to 1500 mV at 20 mV/s with a current of 20 $\mu A$ for 20 scans. A second run in the same range is performed at 200 $\mu A$ scale to grow polymer between the fingers. The parameters are varied depending on the finger width and finger spacing. The result of this step is a chloride ion imprinted polymer.

In step 480, the chloride ions near the surface of the film are expelled by applying a negative voltage to both electrodes while the surface of the film is in contact with a solution. The resulting assembly is consequently imprinted for selective uptake of chloride ions. In some embodiments, step 480 is performed as a last step or sequence of steps with the CS-1200 while in the electrolyte solution of chloride salt and pyrrole species. In some embodiments, step 480 is omitted. In such embodiments, the removal of chloride ions has been determined to be unimportant as the sensors equilibrate in solution to whatever chloride concentration is found.

Figure 5B:
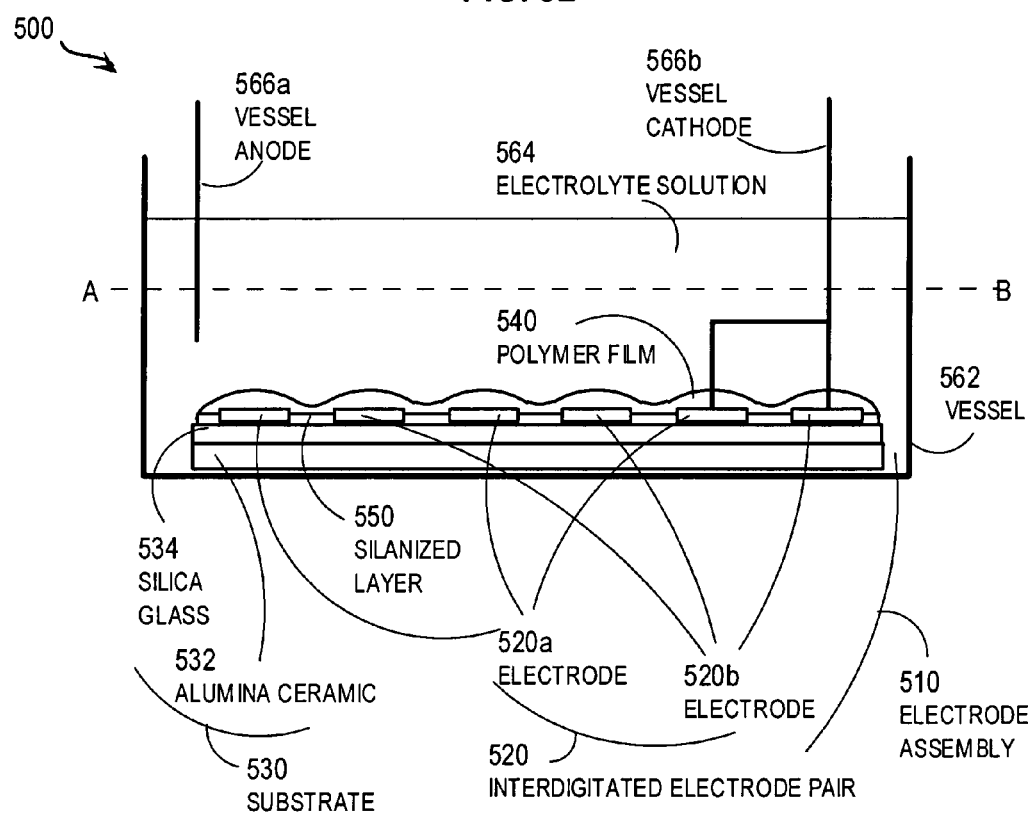
FIG. 5B is a block diagram that illustrates electrochemical polymerization for deposition of a polymer film on the pair of interdigitated electrodes on the substrate, according to an embodiment.

FIG. 5B is a block diagram that illustrates electro-chemical polymerization for deposition of a polymer film on the pair of interdigitated electrodes on the substrate, according to an embodiment. An electrode assembly 510 is placed in a vessel 562 with electrolyte solution 564.

The electrode assembly 510 is shown in cross section along line AB depicted in FIG. 5A. The electrode assembly 510 includes a substrate 530 that includes an alumina ceramic layer 532 of 96% $AlO_2$ and a silica glass layer 534. The electrode assembly 510 also includes the pair of interdigitated electrodes 520 deposited on the silica glass layer 534. The extensions of electrode 520a alternate with extensions of electrode 520b in this cross section along line AB. The electrode assembly 510 differs from the electrode assembly 501 in FIG. 5A by including a silanized layer 550 deposited during the treatment with the silanizing agent in step 420. After onset of the electro-chemical polymerization process, during step 460, the electrode assembly 510 also includes deposited polymer film 540.

The vessel 562 is equipped with a vessel anode 566a and a vessel cathode 566b, collectively referenced hereinafter as vessel electrodes 566. During electro-chemical polymerization in step 470, the vessel anode 566a is in contact with the solution 564 and the vessel cathode 566b is in electrical contact with both electrodes 520a, 520b of the electrode pair 520. The negatively charged cathode attracts positively charged chains of the pyrrole species (nPy or nMPy) to the electrode pair 520. The polymer chains adhere to the negatively charged electrodes 520 and the silanized layer 550. The voltage on the two vessel electrodes 566a, 566b, are cycled to alternate between low and high voltage so that at low voltage, negatively charged chloride ions can bind with the chains of the positively charged pyrrole species (nPy or nMPy) and be incorporated into the film. At sufficiently high voltage, during step 470 or step 480, chloride ions are expelled from the film, leaving empty binding sites imprinted in the polymer film.

4. Conductivity Measurements.

The conductivity of the imprinted polymer electrode assembly as a function of chloride ion concentration is determined for several sample imprinted polymer electrode assemblies fabricated under varying conditions. Results of conductivity tests are shown for measurements in test solutions of differing known concentrations of lithium chloride (LiCl) dissolved in differing concentrations of sodium hydroxide (NaOH). Solutions with LiCl concentrations of $10^{-1}$ M, $10^{-2}$ M, $10^{-2}$ M, $10^{-4}$ M, $10^{-5}$ M and $10^{-6}$ M are prepared. Since there is one chloride ion (Cl—) for each LiCl molecule in solution, the concentrations of the Cl— are the same as the concentrations of the LiCl in units of M. Solutions with pH values of 11, 12, and 13, among others, are prepared for the conductivity tests. The concentration of NaOH determines the pH of some of the solutions. The highest expected pH value that could be obtained in concrete, about 12.65, would be due to $CaOH_2$ and so the highest expected pH test solution is made with a saturated solution of $CaOH_2$.

Solid LiCl and 0.989 normality (N) NaOH volumetric standard are obtained from Aldrich Chemical Company and used to prepare the test solutions. Conductivity measurements are made using a YSI model 32 Conductance Meter manufactured by Yellow Springs Instrument Company of Yellow Springs, Ohio.

FIG. 6A is a graph that illustrates the performance of an imprinted polymer electrode assembly at different pH levels, according to an embodiment. The horizontal axis is a chloride concentration axis 612 in units of the log of the concentration in M; therefore concentrations of $10^{-1}$ M, $10^{-2}$ M, $10^{-2}$ M, $10^{-4}$ M, $10^{-5}$ M and $10^{-6}$ M for the test solutions occur on axis 612 at values of −1, −2, −3, −4, −5, −6, respectively. The vertical axis is a measured electrical conductivity axis 614 in units of micro-mhos (μmho, 1 μmho=$10^{-6}$ mhos).

An imprinted polymer electrode assembly is constructed with gold electrodes on a substrate of silicon glass and alumina ceramic, as described above, under electrochemical polymerization in an electrolyte solution having 1 M LiCl and 0.1 M nMPy. Curve 616a traces the conductivity measured at different concentrations of Cl— in an alkaline solution that has a pH of 11. Curve 616b traces the conductivity measured with the same assembly and concentrations of Cl— in a more alkaline solution that has a pH of 12.

Curves 616a, 616b (collectively referenced hereinafter as curves 616) both show increasing conductivity with increasing Cl— concentration for Cl— concentrations above $10^{-3}$ M. As indicated in Table 1, this is sensitive enough to detect the early progress of conditions that lead to corrosion, before corrosion actually occurs—at $10^{-3}$M sensitivity, 13 degrees of pre-corrosion chloride levels can be determined (from 0.000 M to 0.012 M). The assembly provides greater sensitivity at pH 11, as shown in curve 616a by the continued dependence of conductivity on Cl— concentration down to $10^{-4}$ M and the greater span of conductivity values from about 135 μmhos to about 200 μmhos. It is noted that once concrete cures and achieves a stable pH, even an unknown stable value, a time history of conductivity measured by assemblies with performance like that depicted in curves 616 will indicate a temporal change to a Cl— concentration above $10^{-3}$ M, and therefore will indicate the onset of conditions that lead to corrosion.

Figure 6B:
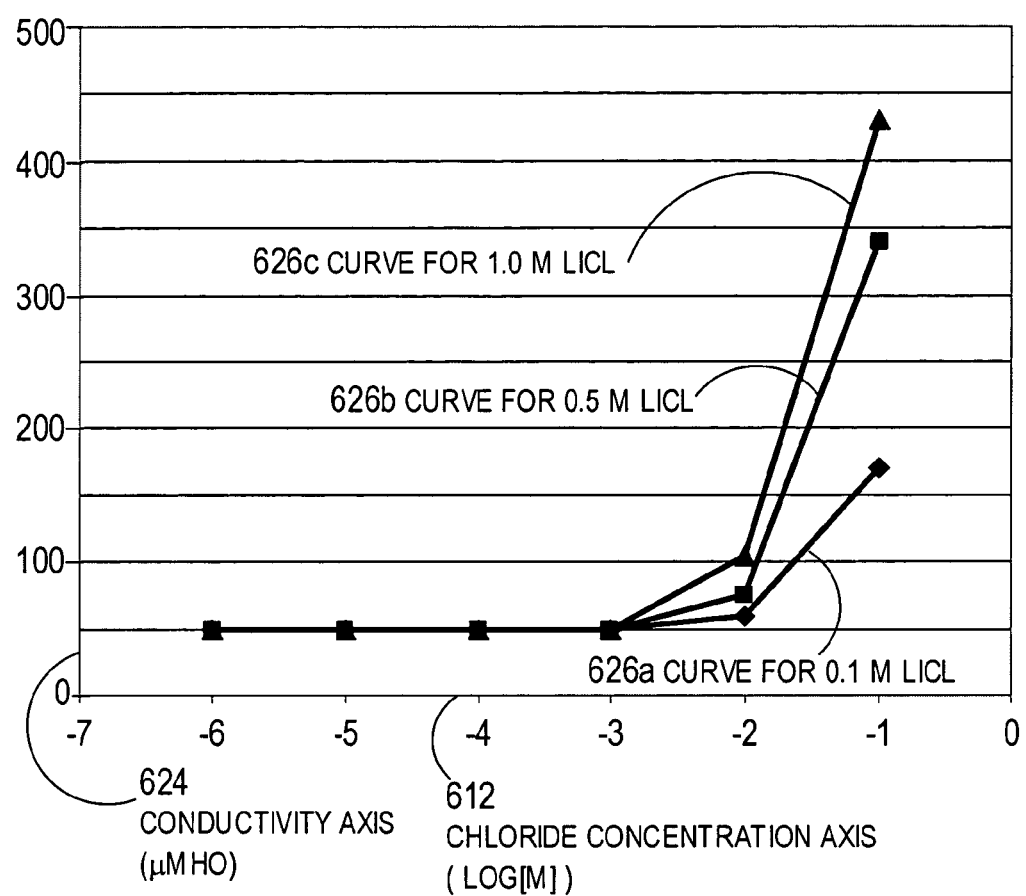
FIG. 6B is a graph that illustrates the performance of chloride ion sensors fabricated with different concentrations of LiCl during polymerization, according to some embodiments.

FIG. 6B is a graph that illustrates the performance of chloride ion sensors fabricated with different concentrations of LiCl during electrochemical polymerization, according to some embodiments. The horizontal axis is a chloride concentration axis 612 in units of the log of the concentration in M; as described above. The vertical axis is a measured electrical conductivity axis 624 in units of μmho, with a greater range than the conductivity axis 614 of FIG. 6A.

Three imprinted polymer electrode assemblies are constructed under electro-chemical polymerization in an electrolyte solution having 0.1 M nMPy and three different concentrations of LiCl. Curve 626a traces the conductivity measured at several concentrations of Cl— with an assembly made with a LiCl concentration of 0.5 M. Curve 626b traces the conductivity measured at those several concentrations of Cl— with an assembly made with a LiCl concentration of 0.5 M. Curve 626c traces the conductivity measured at those several concentrations of Cl— with an assembly made with a LiCl concentration of 1.0 M. These curves are presented to determine the effect of the supporting electrolyte concentration on sensor response. As expected, higher concentrations of chloride in the supporting electrolyte produce polymers with more chloride binding sites and hence a greater response of conductivity to chloride concentration. The substrates were identical for all curves, as were all parameters, except the differing LiCl concentrations Curves 626a, 626b, 626x (collectively referenced hereinafter as curves 626) all show increasing conductivity with increasing Cl— concentration for Cl— concentrations above $10^{-3}$ M. As indicated in Table 1, this is sensitive enough to detect the early progress of conditions that lead to corrosion, before corrosion actually occurs. An assembly provides greater sensitivity as the concentration of LiCl increases in the electrolyte used during electro-chemical polymerization of the assembly. Increased sensitivity is shown in a curve 626 by the greater span of conductivity values compared to a curve for an assembly fabricated with a smaller concentration of LiCl in the electrolyte. For example, curve 626c shows a greater span of conductivity values (almost 400 μmhos from about 50 μmhos to about 430 μmhos) compared to curve 626b for an assembly fabricated with a smaller concentration of LiCl in the electrolyte. It is noted that curve 626c is different from both curves 616 of FIG. 6A because one or more other conditions differ, such as the concentration of the electrolyte and the equilibrium time for the electrochemical polymerization. The curves 616 of FIG. 6A were produced with a device that was made using 0.1 M LiCl and a short equilibrium time; as a result the polymer film is not as thick as in the device used to produce curves 626 in FIG. B.

FIG. 6C is a graph that illustrates the performance of a chloride ion sensor under wet and dry conditions, according to an embodiment. The horizontal axis is a chloride concentration axis 612 in units of the log of the concentration in M; as described above. The vertical axis is a measured electrical conductivity axis 634 in units of μmho, with a greater range than the conductivity axis 614 of FIG. 6A or axis 624 of FIG. 6B.

An imprinted polymer electrode assembly is constructed according to an embodiment of the methods described above. The assembly is constructed using typical industry accepted techniques. The assembly includes a ceramic substrate formed from a 2,000 Angstroms (Å) thin film of silica-dioxide ($SiO_2$) over a polished 99.6% alumina ($Al_2O_3$) that is 0.015 inch thick. The assembly includes patterned conductors formed by 6,000 Å thick layer of sputtered gold over a 500 Å thick layer of sputtered titanium-tungsten on top of the ceramic substrate. Curve 636a traces the conductivity measured at several concentrations of Cl— in a solution. It is noted that curve 636a is different from previous curves 616 and 626 because one or more other conditions differ. Curve 636b traces the conductivity measured with the same assembly at those several concentrations of Cl— after the assembly is removed from the solution and allowed to dry.

Curves 636a, 636b (collectively referenced hereinafter as curves 636) both show increasing conductivity with increasing Cl— concentration for Cl— concentrations above $10^{-3}$ M. As indicated in Table 1, this is sensitive enough to detect the early progress of conditions that lead to corrosion, before corrosion actually occurs. The assembly provides greater sensitivity when wet, as shown in curve 626a by the greater span of conductivity values from about 50 μmhos to about 3700 μmhos. It is noted that it may be desirable in some embodiments to include a moisture sensor to determine whether the film is wet or dry, so that an appropriate curve can be used to transform conductivity measurements to values of Cl— concentration.

5. System for Monitoring Reinforced Concrete Structure.

In some embodiments, a chloride ion sensor is included in a system to monitor the conditions for degradation of a structure. For example, the sensor is included on the Wireless Embedded Sensor Platform (WESP) described in U.S. patent application Ser. No. 10/220,102, filed Aug. 27, 2002 (hereinafter Cain), the entire contents of which are hereby incorporated by reference as if fully set forth herein. When sensors are mounted on the WESP platform, the combination is called a Smart Aggregate.

Figure 7A:
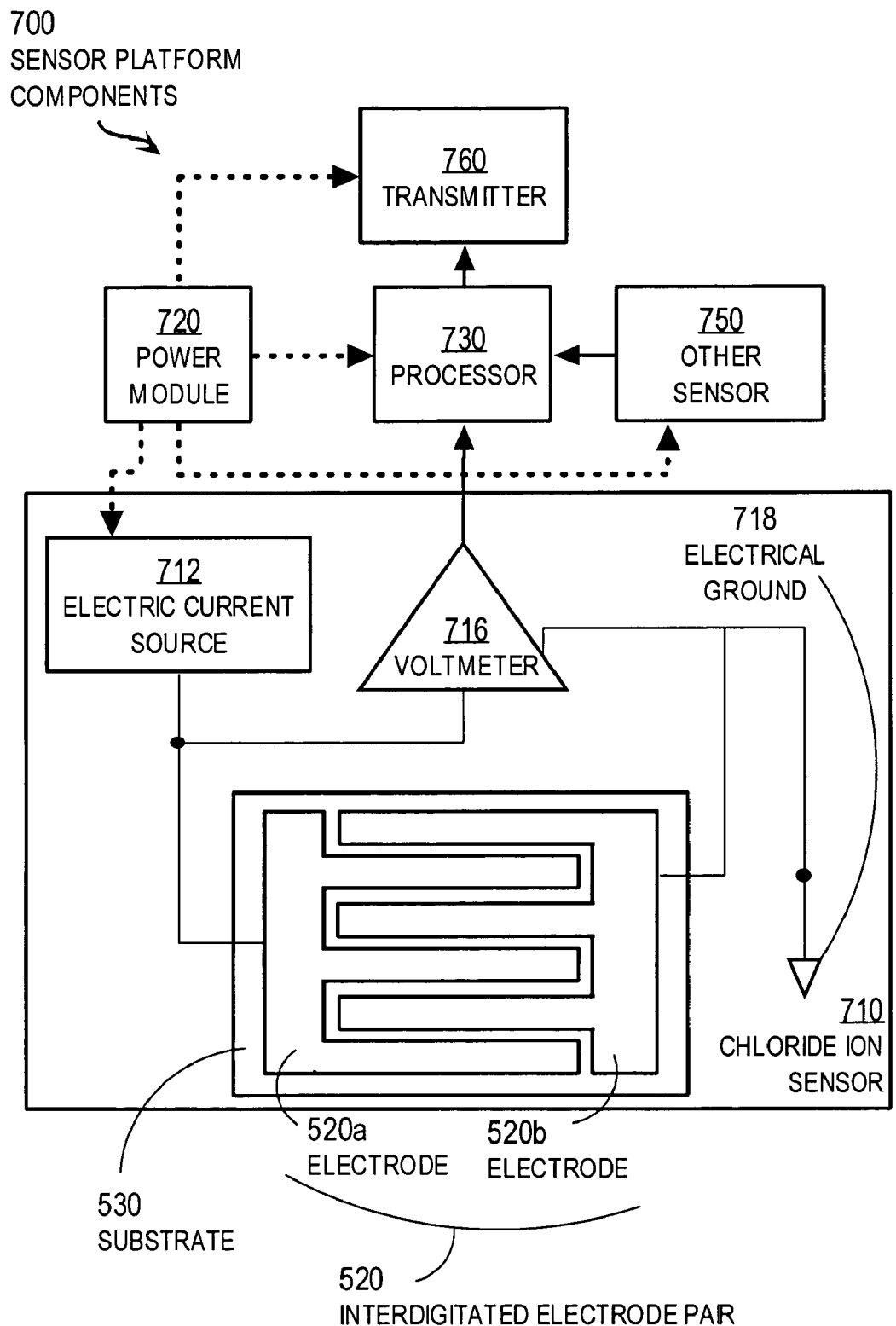
FIG. 7A is a block diagram that illustrates components on a sensor platform to be embedded in a medium for measuring chloride ion concentration, according to an embodiment.

FIG. 7A is a block diagram that illustrates components 700 on a sensor platform to be embedded in a medium for measuring chloride ion concentration, according to an embodiment. In the illustrated embodiment, the components 700 include a chloride sensor 710, a power module 720, a processor 730, another sensor 750 and a transmitter 760, all attached to the sensor platform (not shown).

The power module 720 provides power for the other components, as indicated in FIG. 7A by the broken-line arrows. In an embodiment described in Cain, the power module includes an induction coil and rectifier to receive power from a magnetic pulse transmitted from an interrogation unit outside the structure.

The processor 730 receives information from the chloride ion sensor 710 and any other sensor 750, as indicated by the unbroken arrows in FIG. 7A. The processor 730 computes any derived quantities, and composes a message. The message is provided to the transmitter 760 as indicated by the unbroken arrow.

The transmitter 760 converts the message to an electromagnetic signal and transmits the signal to the interrogation unit.

The chloride ion sensor 710 includes an imprinted polymer electrode assembly, of which the interdigitated electrode pair 520 and substrate 530 are shown in FIG. 7A. The interdigitated electrode pair 520 includes electrode 520a and electrode 520b. The chloride ion sensor 710 also includes electrical components to determine the conductivity of the imprinted polymer electrode assembly. Any method known in the art may be used to determine the conductivity of the assembly. In the illustrated embodiment, the chloride ion sensor 710 also includes an electric current source 712 powered by the power module 720, a voltmeter 716 and electrical ground 718 connected by electrical connections indicated by thin line segments. In other embodiments, different components are included, for example a voltage source and an ammeter are included instead of the current source 712 and voltmeter 716. In some embodiments, one or more of these electrical components are external to the chloride ion sensor 710, or are shared with other components, or both.

In the illustrated embodiment, the current source 712 produces a current of known amperage that travels along electrical connections to electrode 520a of the imprinted polymer electrode assembly. The current passes through the polymer film 540 (not shown) and into electrode 520b. The current then travels along electrical connections through any other chloride circuit components to ground 718. Any electrical components known in the art may be used, such as diodes, resistors, capacitors, to achieve an acceptable reading by the voltmeter 716.

The voltmeter 716 determines the voltage drop across the imprinted polymer electrode assembly during the passage of this current. That voltage drop is related to the conductivity (inverse of the resistance) of the assembly via Ohm's Law, as is well-known in the art. The measured conductivity of the assembly is related to the number of chloride ions that have migrated into the polymer film 540, which in turn, is related to the concentration of chloride ions in the medium when the medium in contact with the polymer film was most recently wet.

The other sensor 750 includes one or more other sensors of the Smart Aggregate. In some embodiments, the other sensor 750 includes a conductivity sensor. In some embodiments, the other sensor 750 includes a temperature sensor. In some embodiments, the other sensor 750 includes a moisture sensor so that the processor 730 can derive chloride ion concentration from conductivity of the assembly using different relationships for wet and dry conditions. In some embodiments, a conductivity sensor is used to determine whether the medium is wet or dry in the vicinity of the sensor platform. In some embodiments, the other sensor 750 is omitted.

FIG. 7B is a block diagram that illustrates an outer face of a sensor platform 770 to be embedded in a medium for measuring chloride ion concentration, according to an embodiment. In the illustrated embodiment, the components 700 of the sensor platform 770 are encapsulated in a ceramic body 778 that only exposes to the medium a pair of conductivity electrodes 772 and the surface of the polymer film 540 of the imprinted polymer electrode assembly. The conductivity electrodes determine the conductivity of the medium by measuring the voltage drop between electrodes 772a and 772b for a known current, or the current that flows between electrodes 772a and 772b in response to a known voltage, or by any other means known in the art.

The imprinted polymer film 540 is exposed to the medium for uptake of Cl— from the medium when and if the medium becomes wet. The amount of Cl— taken up depends on the concentration of Cl— in the medium. The conductivity of the imprinted polymer film depends on the amount of Cl— taken up.

Figure 8:
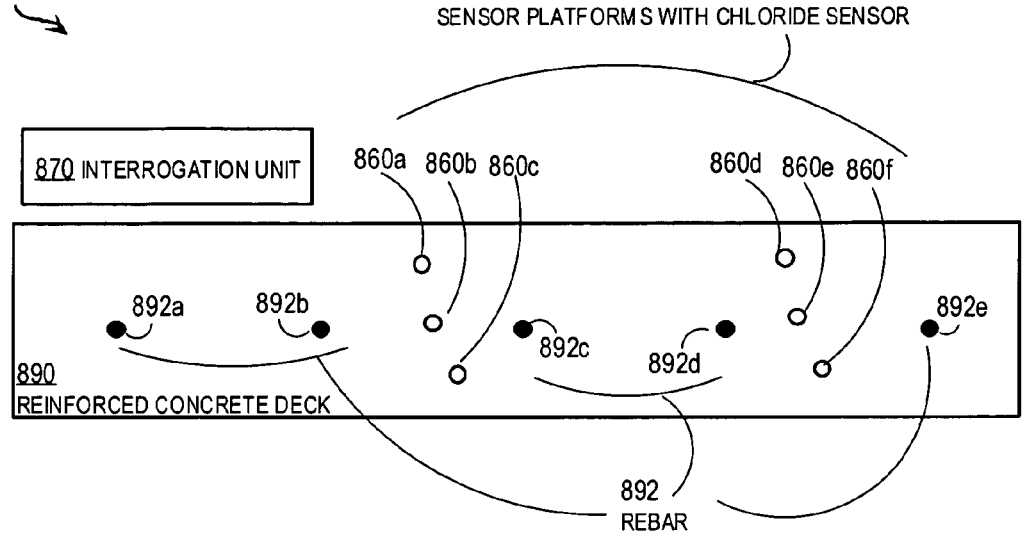
FIG. 8 is a block diagram that illustrates deployment of a system for measuring chloride ion concentration in a medium, according to an embodiment.

FIG. 8 is a block diagram that illustrates deployment of a system 800 for measuring chloride ion concentration in a medium, according to an embodiment. In the illustrated embodiment, the medium is reinforced concrete in a reinforced concrete deck 890 which includes reinforcing bars (rebar) 892 that crisscross in the medium. The cross sections of five rebar 892a, 892b, 892c, 892d, 892e are illustrated.

The deployed system 800 includes sensor platforms 860 embedded in the concrete. Any method for embedding the sensors in the concrete may be used. For example, holes are drilled in an existing structure and one or more sensor platforms are inserted in the holes along with freshly mixed concrete. In another example, the sensors are installed when concrete for the reinforced concrete deck is poured over the rebar. Each sensor platform 860 includes a chloride ion sensor. The position of six sensor platforms 860a, 860b, 860c, 860d, 860e, 860f are illustrated.

The deployed system also includes an interrogation unit 870 which is intermittently passed over the reinforced concrete deck 890 to interrogate the sensors on the sensor platforms 860. In an embodiment using the WESP, the interrogation unit 870 includes a transmitter to transmit an interrogation pulse which provides power to the power module 720 on each sensor platform 860 and a receiver to receive the signals sent by the transmitter 760 on each sensor platform 860. The interrogation unit 870 then passes the received information to an onboard or remote processor for determining the state of processes related to degradation in deck 890.

The progress of degradation in the reinforced concrete deck 890 is monitored by periodically passing the interrogation unit 870 across the surface of the concrete deck 890, recording the measurements from sensors onboard the sensor platforms 860, detecting changes from previous passages, and determining the significance of those changes.

For example, if sensor platforms 860a and 860d, but no others, begin to report detectable levels of Cl—, then it is determined that salt penetration has just begun but only minor preventive action, such as applying sealant to the surface of the deck 890 is called for. However, for example, if sensor platforms 860a and 860b shows significant increases in Cl— concentrations over time, such as Cl— concentrations approaching 1.2 pounds NaCl per cubic yard or more, then it is determined that rebar 892c and perhaps 892b are subject to the onset of corrosion. In this circumstance, some more substantial remedial action may be called for, such as repairing cracks in the deck 890 in the vicinity of sensor platforms 860a, 860b.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A sensor for measuring chloride ion concentration in a medium, comprising:
   a pair of electrodes; and
   a polymer film comprising methylpyrrole imprinted for uptake of chloride ions under alkaline conditions,
   wherein the film is disposed on an electrode of the pair of electrodes for contact with the medium.

2. The sensor as recited in claim 1, wherein the alkaline conditions include a pH range above 7 in the medium.

3. The sensor as recited in claim 1, wherein the alkaline conditions include a pH range from about 10 to about 12.65 in the medium.

4. A sensor for measuring chloride ion concentration in a medium, comprising:
   a pair of electrodes; and
   a polymer film imprinted for uptake of chloride ions under alkaline conditions,
   wherein the polymer film comprises one of
   (i) polypyrrole and polystyrene sulfonate, and
   (ii) poly-methylpyrrole,
   wherein the film is disposed on an electrode of the pair of electrodes for contact with the medium,
   wherein the film is disposed in contact with the pair of electrodes.

5. The sensor as recited in claim 4, further comprising:
   a source of electric current to a circuit including the pair of electrodes; and
   a voltmeter to determine a voltage difference between the pair of electrodes in response to the electric current.

6. The sensor as recited in claim 4, wherein the film is further disposed to lie between the medium and the pair of electrodes.

7. The sensor as recited in claim 4, wherein an electrical conductivity of the film depends on an amount of chloride ions taken up by the film.

8. The sensor as recited in claim 4, wherein the pair of electrodes comprises a pair of interdigitated electrodes.

9. A sensor for measuring chloride ion concentration in a medium, comprising:
   a pair of electrodes; and
   a polymer film imprinted for uptake of chloride ions under alkaline conditions,
   wherein the film is disposed on an electrode of the pair of electrodes for contact with the medium,
   wherein the film is disposed in contact with the pair of electrodes, and
   wherein the pair of electrodes comprises gold electrodes.

10. A sensor for measuring chloride ion concentration in a medium, comprising:
    a pair of electrodes; and
    a conductive polymer film imprinted for uptake of chloride ions under alkaline conditions,
    wherein
    the polymer film comprises one of
    (i) methylpyrrole,
    (ii) polypyrrole and polystyrene sulfonate, and
    (iii) poly-methylpyrrole,
    the film is disposed in contact with the pair of electrodes,
    the film is disposed for contact with the medium, and
    an electrical conductivity of the film depends on an amount of chloride ions taken up by the film.

11. The sensor as recited in claim 10, wherein a measurable change in electrical conductivity occurs for a chloride ion concentration change of less than 0.02 percent by weight in a chloride ion concentration range from about 0.01 percent by weight to about 0.05 percent by weight.

12. The sensor as recited in claim 10, wherein a measurable change in electrical conductivity occurs for a chloride ion concentration change of less than 0.01 percent by weight in a chloride ion concentration range from about 0.02 percent by weight to about 0.04 percent by weight.

13. The sensor as recited in claim 10, wherein a minimum detectable chloride ion concentration is about 0.00013 percent by weight.

14. The sensor as recited in claim 10, wherein a measurable change in electrical conductivity occurs for a chloride ion concentration change of less than 0.02 percent by weight in a chloride ion concentration range above about 0.02 percent by weight in a medium with a pH up to at least 12.65.

15. An apparatus for long term monitoring of chloride ion concentration in a medium, comprising:
a sensor platform for embedding in a medium;
a transmitter disposed on the sensor platform for transmitting to an interrogation unit a response signal based on a chloride measurement; and
a chloride sensor disposed on the sensor platform, which chloride sensor generates the chloride measurement, said chloride sensor comprising
a pair of electrodes, and
a conductive polymer film imprinted for uptake of chloride ions under alkaline conditions,
wherein
the film is disposed in contact with the pair of electrodes,
the film is disposed for contact with the medium, and
an electrical conductivity of the film depends on an amount of chloride ions taken up by the film.

16. The apparatus as recited in claim 15, wherein,
the apparatus further comprises a power module disposed on the platform, which power module is powered by an interrogation pulse transmitted by the interrogation unit; and
the transmitter and the chloride sensor are powered by the power module.

17. The apparatus as recited in claim 15, wherein:
the apparatus further comprises a conductivity sensor disposed on the platform for generating an electrical conductivity measurement of the medium; and
the response signal is further based on the conductivity measurement.

18. The apparatus as recited in claim 17, wherein:
the apparatus further comprises a processor disposed on the sensor platform, which processor derives a moisture-corrected chloride measurement based on the chloride measurement and the conductivity measurement; and
the response signal is based on the moisture-corrected chloride measurement.

19. A method for fabricating a sensor for measuring chloride ion concentration in a medium, the method comprising the steps of:
depositing an electrode on a substrate;
after said step of depositing the electrode, placing the substrate in an electrolyte solution of lithium chloride and methylpyrrole;
after said step of placing the substrate in the electrolyte solution, applying cyclic voltammetry to form a polymer film in contact with the electrode.

20. The method as recited in claim 19, wherein,
said step of depositing the electrode on the substrate further comprises depositing a pair of electrodes on the substrate;
the method further comprising, before said step of placing the substrate in the electrolyte solution, performing the step of treating the substrate with a silanizing agent to enhance adherence of a pyrrole species to the substrate between the pair of electrodes.

21. The method as recited in claim 20, said step of treating the substrate with a silanizing agent further comprising treating the substrate with a silanizing agent that comprises silica and pyrrole.

22. The method as recited in claim 20, said step of depositing the pair of electrodes on the substrate further comprising depositing gold electrodes on the substrate.

23. The method as recited in claim 20, said step of depositing the pair of electrodes on the substrate further comprising depositing a pair of interdigitated electrodes on the substrate.

24. The method as recited in claim 19, further comprising, before said step of depositing an electrode on the substrate, performing the step of forming the substrate by depositing silica glass on an alumina ceramic plate.

\* \* \* \* \*